(12) United States Patent
Oldham

(10) Patent No.: US 6,236,890 B1
(45) Date of Patent: May 22, 2001

(54) STIMULATION OF MUSCLES

(75) Inventor: Jacqueline A. Oldham, Liverpool (GB)

(73) Assignee: The Victoria University of Manchester, Manchester (GB)

(*) Notice: Subject to any disclaimer, the term of this patent is extended or adjusted under 35 U.S.C. 154(b) by 0 days.

(21) Appl. No.: 09/202,289
(22) PCT Filed: Jun. 11, 1997
(86) PCT No.: PCT/GB97/01565
§ 371 Date: Apr. 28, 1999
§ 102(e) Date: Apr. 28, 1999
(87) PCT Pub. No.: WO97/47357
PCT Pub. Date: Dec. 18, 1997

(30) Foreign Application Priority Data

Jun. 13, 1996 (GB) .................................. 9612388
Oct. 25, 1996 (GB) .................................. 9622267
Nov. 23, 1996 (GB) .................................. 9624386

(51) Int. Cl.$^7$ ..................................... A61N 1/32
(52) U.S. Cl. ............................... 607/68; 607/48
(58) Field of Search ................. 607/48, 49, 68, 607/70, 72, 66

(56) References Cited

U.S. PATENT DOCUMENTS

| | | |
|---|---|---|
| 4,177,819 | 12/1979 | Kofsky et al. . |
| 4,528,984 | 7/1985 | Morawetz et al. . |
| 4,535,777 | 8/1985 | Castel . |
| 4,712,558 | 12/1987 | Kidd et al. . |
| 4,719,922 | 1/1988 | Padjen et al. . |
| 5,018,524 * | 5/1991 | Gu et al. .................................. 607/68 |
| 5,097,833 * | 3/1992 | Campos .................................. 607/72 |
| 5,285,781 | 2/1994 | Brodard . |
| 5,350,415 | 9/1994 | Cywinski . |
| 5,433,737 | 7/1995 | Aimone . |
| 5,504,420 | 4/1996 | Hamard et al. . |
| 5,507,788 | 4/1996 | Lieber . |
| 5,562,718 | 10/1996 | Palermo . |

FOREIGN PATENT DOCUMENTS

| | | |
|---|---|---|
| 1527908 | 10/1978 | (GB) . |
| 2156682 | 10/1985 | (GB) . |
| 2092004 | 1/1988 | (GB) . |
| 2175806 | 9/1988 | (GB) . |
| WO 87/00760 | 2/1987 | (WO) . |

OTHER PUBLICATIONS

Oldham et al, "Rehabilitation of Atrophied Muscle in the Rheumatoid Arthritic Hand: A Comparison of Two Methods of Electrical Stimulation", *The Journal Of Hand Surgery*, (British vol. 1989) 14B:294–297.

Oldham, "Electrotherapeutic Rehabilition of the Quadriceps in Elderly Osteoarthritic Patients: A Double Blind Assessment of Patterned Neuromuscular Stimulation", Clinical Rehabilition 1995: 9:10–20.

Petterson et al, "The Use of Pattened Neuromuscular Stimulation to Improve Hand Function Following Surgery for Ulnar Neuropathy", *Journal Of Hand Surgery* (British and European vol., 1994), 19B:4:430–433.

* cited by examiner

Primary Examiner—George R. Evanisko
(74) Attorney, Agent, or Firm—Nixon & Vanderhye P.C.

(57) ABSTRACT

A muscle stimulator for improving muscle strength and/or endurance. Stimulating pluses are applied to the muscle, the pattern of pulses including a first component in the form of a continuous train of pulses at a first pulse repetition frequency of, for example, between 1 and 6 Hz; a second component in the form of a series of pulse trains at a second pulse repetition frequency of, for example, 40 to 60 Hz; and a third component in the form of a pair of pulses at a third pulse repetition frequency of, for example, 120 to 200 Hz.

22 Claims, 1 Drawing Sheet

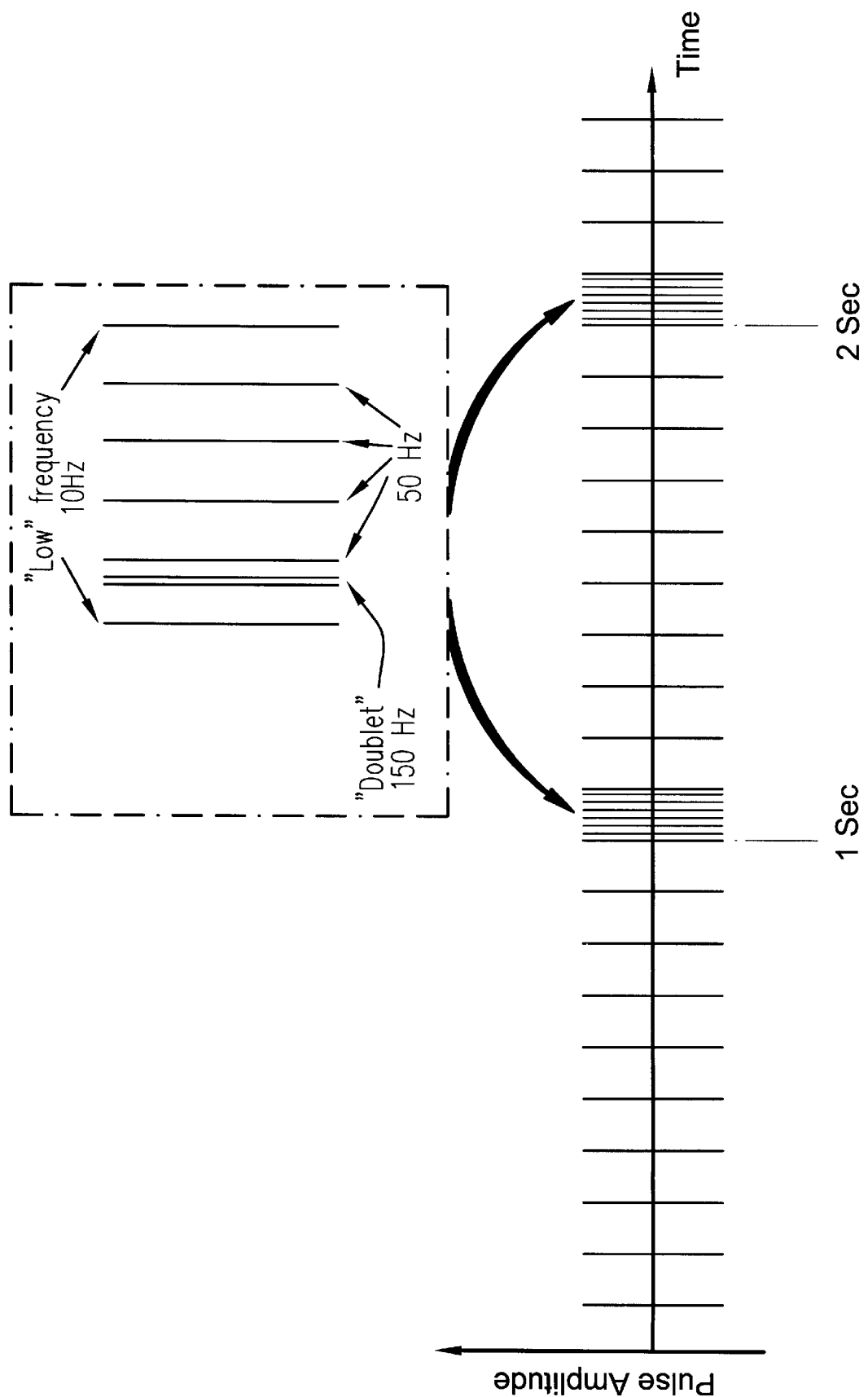

STIMULATION OF MUSCLES

BACKGROUND OF THE INVENTION

The present invention relates to an apparatus and method for the electrical stimulation of muscle which rely upon a particular pattern of electrical stimulation.

It is well known that muscle contraction is caused by neural stimulation. Contraction occurs when an action potential is conducted down a nerve to a neuromuscular junction, the signal is then communicated to muscle cells and leads to the stimulation of the release of calcium ions into the cytoplasm of muscle cells which thereby modifies interactions between contractile proteins resulting in muscular contraction.

It has been long established that the application of an electrical field to muscles results in an artificially induced contraction of said muscles. Furthermore, as well as directly causing muscular contraction, electrical stimulation at specific frequencies can also modify the phenotype of a muscle. For instance, prolonged stimulation of a fast-twitch muscle with a uniform frequency of 10 Hz results in the fast-twitch muscle developing slow-twitch characteristics, namely increased endurance, but with less power than would be normal for fast-twitch muscle. Conversely, prolonged stimulation of a slow-twitch muscle with an intermittent frequency of 30–50 Hz results in the slow-twitch muscle developing fast-twitch characteristics, namely increased power, but with less endurance than would be normal for slow-twitch muscle.

It has been suggested that electrical stimulation of muscles may be a useful means of improving strength and/or endurance of incapacitated muscle (due to injury, under-use or some pathological condition). For a number of years muscles have been stimulated by Faradic stimulation delivering uniform frequencies (of around 30–50 Hz) with the aim of beneficially affecting the muscle. However, these treatments have at best been ineffective and at the worst harmful to the muscle in the long term.

UK Patent GB 2 156 682 examined the electrical discharge of nerves innervating muscle with an aim of developing a means of beneficially stimulating muscle. It discloses a method of recording electrical discharges from nerves innervating muscles. A signal generated on the basis of the recording is then used to "electrotrophically" stimulate muscle. Electrotrophic stimulation is defined as "the electrical stimulation of muscle fibre using a stimulating signal containing information effective to cause structural and/or functional change of muscle fibre without requiring the muscle fibre to respond mechanically to the stimulation". However the stimulating signal of GB 2 156 682 is complex and difficult to generate.

BRIEF SUMMARY OF THE INVENTION

It is an object of the present invention to provide an improved apparatus and method for electrically stimulating a muscle to improve strength and endurance of the muscle.

According to the present invention there is provided an electrical muscle stimulator including means for generating a stimulating signal comprising a first component in the form of a train of pulses at a first pulse repetition frequency, a second component in the form of a series of pulse trains at a second pulse repetition frequency higher than the first, and a third component in the form of a pair of pulses at a third pulse repetition frequency higher than the second pulse repetition frequency, each pail of pulses being coupled with a respective train of pulses of the second component.

The invention also provides a method for electrically stimulating a muscle in which a stimulating signal is applied to the muscle, the stimulating signal including a first component in the form of a train of pulses at a first pulse repetition frequency, a second component in the form of a series of pulse trains at a second pulse repetition frequency higher than the first, and a third component in the form of a pair of pulses at a third pulse repetition frequency higher than the second pulse repetition frequency, each pair of pulses being coupled with a respective train of pulses of the second component.

It is preferred that the first pulse repetition frequency is between 1 and 15 Hz, for example between 1 and 6 Hz or between 5 and 15 Hz. It is also preferred that the second pulse repetition frequency is between 30 and 60 Hz, for example between 40 and 60 Hz and the third pulse repetition frequency is between 120 and 300 Hz, for example between 120 and 200 Hz.

The inventor believes that stimulation of muscle with the electrical signal of the invention is of great benefit in the rehabilitation oft regeneration of or prevention of atrophy of skeletal muscle. Inspiration for the invention has arisen from the examination of electrical discharge from nerves innervating muscle. It has been established that certain signals cause muscular contraction and also have unexpected beneficial effects on muscular strength and endurance.

BRIEF DESCRIPTION OF THE FIGURES

An embodiment of the invention will now be described, by way of example, with reference to the accompanying drawing.

DETAILED DESCRIPTION OF EXEMPLARY EMBODIMENTS

The attached drawing illustrates one pulse pattern generated in an electrical muscle stimulator in accordance with the invention. It will be noted that pulses are generated at regular intervals of 0.1 second such that the pulse pattern incorporates a continuous 10 Hz first component. At periodic intervals this continuous relatively low frequency component is combined with short bursts of a higher frequency second component, in the illustrated case a series of four pulses at 0.2 second intervals such that the pulse repetition rate of the second components corresponds to 50 Hz. In addition, a third component in the form of a "doublet" of pulses is coupled with the second component, in the illustrated case the spacing between the two pulses of the doublet is 0.0066 seconds representing a pulse repetition rate of 150 Hz. It will be noted that in the illustrated case the third component immediately precedes the second component, although its position relative to the second component may differ from that shown in this example.

All of the pulses represented in the accompanying drawing are of identical structure, each pulse including positive and negative-going components. Pulse shapes such as used in conventional muscle stimulation equipment may be used, the advantages of the invention arising from the pattern of such pulses rather than of the shape of individual pulses.

Good results have been achieved using the pattern of pulses represented in the drawing. It is believed however that a further improvement can be achieved by reducing the frequency of the low frequency component from 10 Hz as shown to 6 Hz or below.

It is believed that a course of treatment relying upon the described pulse pattern could be for one to three hours per day every day over a six to eight week period. The pulses could be applied to any muscle throughout the body via simple self adhesive electrodes. The pulses could be applied for "on" times of from ten to fifty seconds, with periods of inactivity, i.e. "off" times, of approximately the same duration. Good results have been obtained with "on" times of ten seconds in combination with "off" times of fifty seconds.

What is claimed is:

1. An electrical muscle stimulator comprising:
   means for generating a stimulating signal, said signal including
   (i) a first component as a first continuous train of regularly spaced pulses,
   (ii) a second component as a series of regularly spaced second trains of regularly spaced pulses, wherein the second component is combined with the first component and spacing between successive pulses in the second pulse trains is less than the spacing between successive pulses in the first train, and
   (iii) a third component as a series of third trains of pulses, each train consisting of a doublet of only two pulses, spacing between the pulses in each of the third pulse trains being less than the spacing between successive pulses in each of the second trains, and each third pulse train being coupled with a respective second pulse train, and
   a means for applying the signal to a muscle.

2. The electrical muscle stimulator according to claim 1, wherein the spacing between successive pules of the first train is between 66.7 milliseconds (ms) and 1 second (s).

3. The electrical stimulator according to claim 1, wherein the spacing between successive pulses of the first train is between 0.167 s and 1 s.

4. The electrical muscle stimulator according to claim 1, wherein the spacing between successive pulses of the first train is between 66.7 ms and 0.2 s.

5. The electrical muscle stimulator according to claim 1, wherein the spacing between successive pulses of the second train is between 16.7 ms and 33.3 ms.

6. The electrical muscle stimulator according to claim 1, wherein the spacing between successive pulses of the second train is between 25 ms and 16.6 ms.

7. The electrical muscle stimulator accordingly to claim 1, wherein the spacing between the pulses of the third train is between 3.33 ms and 8.33 ms.

8. The electrical muscle stimulator according to claim 1, wherein the spacing between the pulses of the third train is between 5 ms and 8.33 ms.

9. An electrical stimulator as in claim 1 wherein said second and third components are each discontinuous pulse trains comprising periodic spaced-apart bursts of plural regularly spaced pulses within each burst.

10. A method for electrically stimulating a muscle in which a stimulating signal is applied to the muscle comprising:
    a) generating the stimulating signal, the signal including
    (i) a first component as a first continuous train of regularly spaced pulses,
    (ii) a second component as a series of regularly spaced second trains of regularly spaced pulses, wherein the second component is combined with the first component and the spacing between successive pulses in the second pulse trains is less than the spacing between successive pulses in the first train, and
    (iii) a third component as a series of third trains of pulses each train consisting of a doublet of only two pulses, the spacing between the pulses in each of the third pulse trains being less than the spacing between successive pulses in each of the second trains, and each third pulse train being coupled with a respective second pulse train, and
    b) applying the stimulating signal to the muscle.

11. A method as in claim 10 wherein the step of generating the stimulating signal further comprises generating uniformly structured pulses in said first, second and third pulse trains.

12. A method as in claim 10 wherein the step of generating the stimulating signal further comprises generating positive and negative components for each pulse in said first, second and third pulse trains.

13. A method as in claim 10 wherein the step of generating the stimulating signal further comprises having the third component immediately precede the second component.

14. A method as in claim 10 wherein said second and third components are each discontinuous pulse trains comprising periodic spaced-apart bursts of plural regularly spaced pulses within each burst.

15. An electrical muscle stimulator comprising:
    means for generating an electrical muscle stimulating signal including:
    (i) a continuous first train of regularly spaced pulses occurring at a rate of X pulses per second;
    (ii) a discontinuous second train of regularly spaced pulses combined with said first train and occurring at a rate of Y pulses per second, said discontinuous second train comprising regularly spaced-apart bursts or pulse groups with more than two pulses in each burst or group; and
    (iii) a discontinuous third train of regularly spaced pulses occurring at a rate of Z pulses per second, said discontinuous third train comprising regularly spaced-apart bursts or pulse groups with only two pulses in each burst or group,
    wherein $X<Y<Z$;
    each of said third train bursts or groups being coupled to a respectively corresponding one of said second train bursts or groups such that the second and third bursts occur at a common burst repetition frequency; and
    means for applying the signal to a muscle.

16. A muscle stimulator as in claim 15 wherein $X=Y/5=Z/15$.

17. A muscle stimulator as in claim 15 wherein no individual pulses of said trains occur simultaneously.

18. A muscle stimulator as in claim 15 wherein all pulses of each second train burst (i) occur between a pair of pulses in the first train and (ii) are separated from each other second train burst by more than one pair of first train pulses.

19. A method for electrically stimulating muscle comprising:

a) generating an electrical muscle stimulating signal including:

(i) a continuous first train of regularly spaced pulses occurring at a rate of X pulses per second;

(ii) a discontinuous second train of regularly spaced pulses combined with said first train and occurring at a rate of Y pulses per second, said discontinuous second train comprising regularly spaced-apart bursts or pulse groups with more than two pulses in each burst or group; and (iii) a discontinuous third train of regularly spaced pulses occurring at a rate of Z pulses per second, said discontinuous third train comprising regularly spaced-apart bursts or pulse groups with only two pulses in each burst or group;

wherein $X<Y<Z$;

each of said third train bursts or groups being coupled to a respectively corresponding one of said second train bursts or groups such that the second and third bursts occur at a common burst repetition frequency; and b) applying the signal to a muscle.

20. A method as in claim 19 wherein $X=Y/5-Z/15$.

21. A method as in claim 19 wherein no individual pulses of said trains occur simultaneously.

22. A method as in claim 19 wherein all pulses of each second train burst (i) occur between a pair of pulses in the first train and (ii) are separated from each other second train burst by more than one pair of first train pulses.

* * * * *